United States Patent

Bayer et al.

Patent Number: 5,403,730
Date of Patent: Apr. 4, 1995

[54] **PROCESS FOR THE SELECTIVE DEACTIVATION OF ESTERASES AND CATALASES IN *TRIGONOPSIS VARIABILIS* CELLS BY MICROWAVE HEATING WHILE RETAINING D-AMINO ACID OXIDASE ACTIVITY**

[75] Inventors: Thomas Bayer, Bad Soden; Ulrich Holst, Niedernhausen; Uwe Wirth, Mainhausen, all of Germany

[73] Assignee: Hoechst Aktiengesellschaft, Frankfurt am Main, Germany

[21] Appl. No.: 145,167

[22] Filed: Nov. 3, 1993

[30] Foreign Application Priority Data

Nov. 5, 1992 [DE] Germany ............... 42 37 373.5

[51] Int. Cl.$^6$ ............... C12N 13/00; C12N 9/99; C12N 9/06
[52] U.S. Cl. ............... 435/173.2; 435/173.1; 435/184; 435/191; 530/427
[58] Field of Search ............... 435/173.1, 173.2, 184, 435/191, 911; 530/427

[56] References Cited

U.S. PATENT DOCUMENTS

| | | | |
|---|---|---|---|
| 3,801,458 | 4/1974 | Fildes et al. | 435/47 |
| 4,639,375 | 1/1987 | Tsai | 426/49 |
| 4,831,012 | 5/1989 | Estep | 514/6 |
| 5,208,155 | 5/1993 | Mosbach et al. | 435/191 |

OTHER PUBLICATIONS

Ganibov et al. (1990) *Successes in Modern Biology* 110(2/5), 306–320, (in Russian) and English Translation).

*Primary Examiner*—Douglas W. Robinson
*Assistant Examiner*—Jon P. Weber
*Attorney, Agent, or Firm*—Finnegan, Henderson Farabow, Garrett & Dunner

[57] ABSTRACT

Microwave heating of intact *Trigonopsis variabilis* cells to 60°–68° C. for 20–40 seconds selectively deactivates esterases and catalases while retaining the activity of D-amino acid oxidase. The heating is effected with a microwave frequency of 0.4–24 GHz.

4 Claims, No Drawings

PROCESS FOR THE SELECTIVE DEACTIVATION OF ESTERASES AND CATALASES IN *TRIGONOPSIS VARIABILIS* CELLS BY MICROWAVE HEATING WHILE RETAINING D-AMINO ACID OXIDASE ACTIVITY

DESCRIPTION

Process for the selective deactivation of undesired proteins in a protein mixture by means of microwave irradiation.

It has already been disclosed in DE 4,006,436 that proteins can be purified selectively by means of microwave irradiation. However, in the patent specification mentioned, the microorganisms in question are first broken up, and the resulting protein mixture is subsequently heated by means of microwave irradiation.

Surprisingly, it has now emerged that considerable advantages can be achieved by a different procedure. This different procedure comprises subjecting a suspension of largely intact cells to a heating step by means of microwave irradiation, which means that the above-mentioned heating step is carried out before the cells are broken up. Unexpectedly, this procedure results in a highly selective denaturation while simultaneously facilitating the subsequent breaking up of the cells.

Accordingly, the invention relates to a process for the selective deactivation of undesired proteins in a protein mixture by heating by means of microwave irradiation, which comprises subjecting a suspension of largely intact cells to a heating step by means of a microwave irradiation. The term largely intact cells is to be understood in this connection as meaning that the microorganisms are in intact form in the process according to the invention, apart from the cells which have inevitably broken up during the fermentation process, which only account for a small fraction. This means, in particular, that in the process according to the invention, no measures which result in broken up cells are taken before the heating step by means of microwave irradiation.

The process according to the invention is carried out taking into consideration the protein mixture in question and the desired proteins (the proteins not to be deactivated) at a temperature in combination with a specific residence time, where, under the selected conditions, the desired proteins are just about not deactivated, but the undesired proteins are largely denaturated. For example, in the case of Trigonopsis variabilis, the optimum temperature for denaturating esterases and catalases while retaining D-amino acid oxidase, is in a range from 60°-85° C. at a residence time of 10-40 seconds; particularly preferred is a temperature of 65°-75° C. at a residence time of 15-25 seconds, especially a temperature of approximately 70° C. at a residence time of approximately 20 seconds. The effectiveness and selectivity of the process according to the invention can be increased further by subjecting the cell suspension in question to a plurality of heating cycles by means of microwave irradiation under exactly defined conditions.

The process according to the invention can be carried out using various microwave apparatuses. A microwave frequency of 0.4–24 GHz, in particular of 0.4–2.5 GHZ, is preferably used. Microwave frequencies of approximately 433 MHz, 915 MHz and 2.45 GHz are very particularly preferred. It is preferred to use a microwave flow heater, optionally with a holding zone arranged downstream. The working parameters (laminar or turbulent flow, use of mixers and the like) depend on the apparatuses used in each case and must be optimized in each case in such a way that all of the suspension to be treated is heated under defined constant conditions while avoiding temperature and residence time gradients. Technical characteristics of the apparatus and details of the procedure can be found in the above-mentioned patent specification and in the literature cited therein.

The process according to the invention is, for example, particularly suitable for the selective deactivation of esterases and catalases while retaining the activity of D-amino acid oxidase in Trigonopsis variabilis cells.

Furthermore, the step according to the invention is particularly suitable for an economic procedure in which the cell suspension is heated as described directly after the fermentation without working-up steps; surprisingly, constituents and solids in the culture liquid cause no complications.

After the heating process according to the invention, the microorganisms can be worked up by prior-art methods, where, as already mentioned above, breaking up of the cells is facilitated by the microwave treatment.

The present invention shall be illustrated in greater detail by the use examples which follow and by the contents of the patent claims.

EXAMPLE

Experimental set-up:

By means of a gear pump, the cell suspension is pumped from a stirred vessel into a microwave oven. The temperature of the product is measured immediately after it has left the microwave zone. To allow the cell suspension to be kept for the desired period of time at the set temperature, a well insulated holding zone with suitable dimensions is arranged downstream. In a cooler, the cell suspension is subsequently cooled to room temperature and collected in a collecting vessel.

The microwave source used is, for example, a laboratory microwave unit MLS 1200, manufactured by Büchi. To be able to feed the product through the unit, its side walls are provided with in each case one opening.

To achieve higher depletion rates, it may be expedient to subject the cell suspension to repeated heating.

The test results are shown in the table below:

TABLE 1

Change in enzyme activities upon repeated heating (run 1-3) of the cell suspension $T_{max}$ = 70° C., residence time = 20 seconds

|  | D-Amino acid oxidase [%] | Esterases [%] | Catalases [%] |
|---|---|---|---|
| Blank value (before run 1) | 100 | 100 | 100 |
| Run 1 | 100 | 13.0 | 56 |
| Run 2 | 81.8 | 7.3 | 36 |
| Run 3 | 82.0 | 5.5 | 28 |

We claim:

1. A process for the selective deactivation of esterases and catalases contained by *Trigonopsis variabilis* cells which comprises subjecting a suspension of essentially intact *Trigonopsis variabilis* cells to heating at 60°-85° C. for 10-40 seconds by means of microwave irradiation at a microwave frequency of 0.4–24 GHz, whereby the esterases and catalases in the *Trigonopsis variabilis* cells are deactivated while retaining 82 to 100% of the activity of D-amino acid oxidase.

2. The process as claimed in claim 1, wherein a microwave frequency of 0.4 to 2.5 GHz is used.

3. The process as claimed in claim 1, wherein the heating step is at 65°–75° C. for 15–25 seconds.

4. The process as claimed in claim 1, wherein the heating step is at about 70° C. for about 20 seconds.

* * * * *